United States Patent [19]

Wirtschafter et al.

[11] 3,952,735
[45] Apr. 27, 1976

[54] EYE BANDAGE

[76] Inventors: Jonathan D. Wirtschafter, 1147 Athenia Drive, Lexington, Ky. 40504; Juan L. Zauberman, 26 Ben Maimon St.; Samuel Moscowitz, c/o School of Applied Science, Hebrew University of Jerusalem, both of Jerusalem, Israel

[22] Filed: May 27, 1975

[21] Appl. No.: 580,885

[52] U.S. Cl. .............................. 128/163; 128/132 R
[51] Int. Cl.² ................................. A61F 13/12
[58] Field of Search ................. 128/163, 76.5, 76 R, 128/132 R, 97, 402, 403, 275.1, 380; 2/15; 206/440

[56] References Cited
UNITED STATES PATENTS

| | | | |
|---|---|---|---|
| 377,835 | 2/1888 | Lyman et al. ............................. | 2/15 |
| 3,092,103 | 6/1963 | Mower ............................ | 128/132 R |
| 3,762,419 | 10/1973 | Walters ............................... | 128/403 |
| 3,768,485 | 10/1973 | Linick ............................... | 128/402 |

*Primary Examiner*—Lawrence W. Trapp
*Attorney, Agent, or Firm*—Mason, Fenwick & Lawrence

[57] ABSTRACT

A pneumatic eye bandage is disclosed having an adhesive coated portion for attachment to the area surrounding the eyelid of the user, a pneumatic cushion composed of a closed cell or multi-cells which may be contoured to conform to the eye of the user or may be contoured to provide a desired pressure distribution on the eye of the user, said cells are intermediate the overlying bandage and the eye of the user and may optionally be provided with adhesive areas and adsorbent pads on the pneumatic cushion to prevent movement of the eyelid of the user and collect discharges from the eye.

19 Claims, 14 Drawing Figures

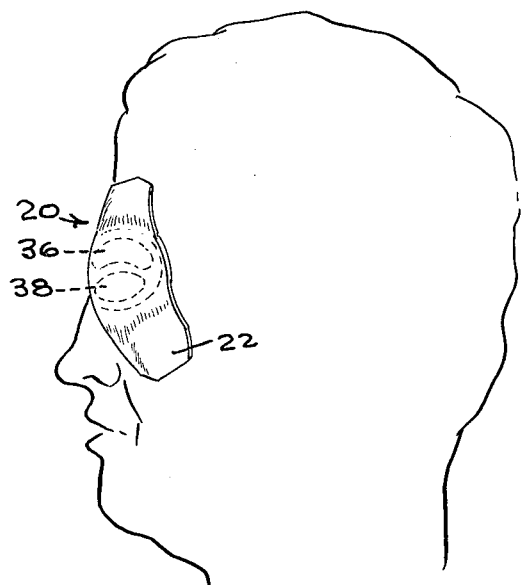
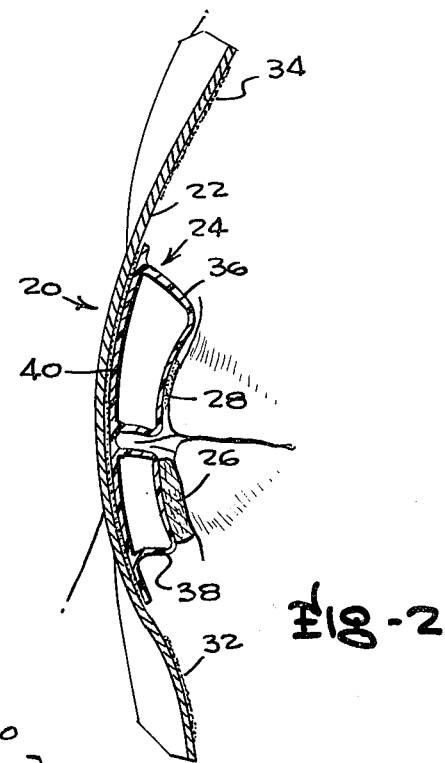
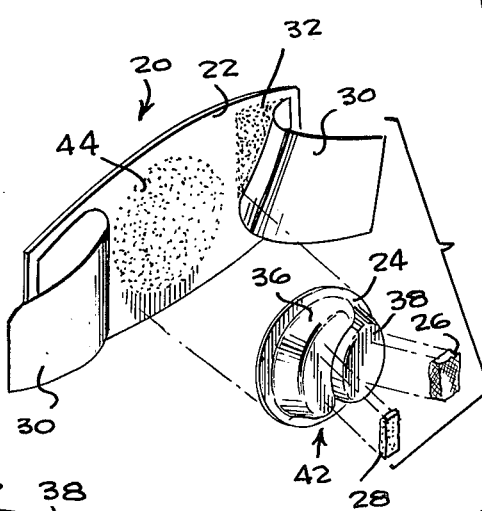
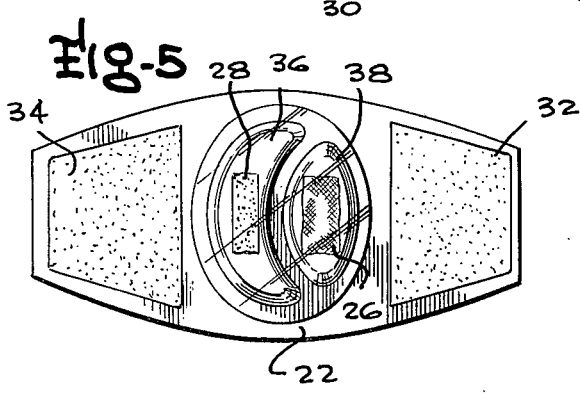
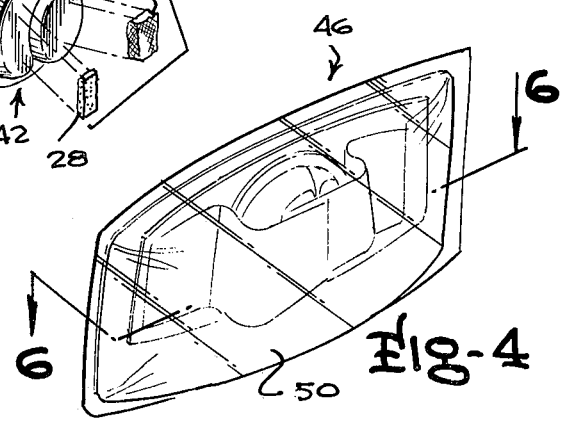
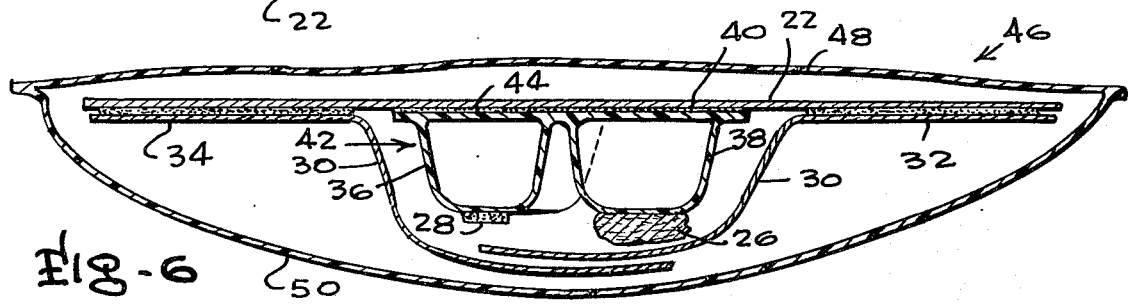

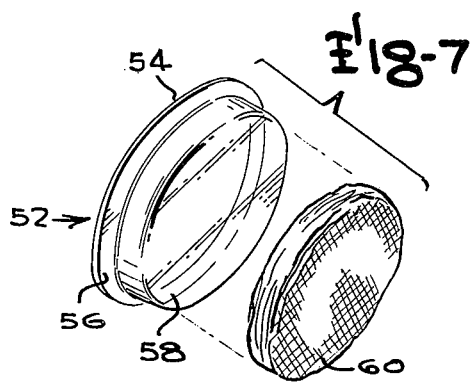
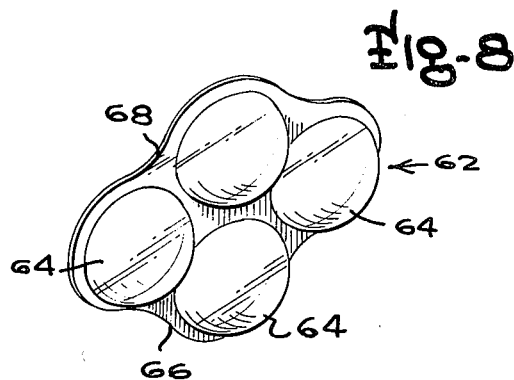
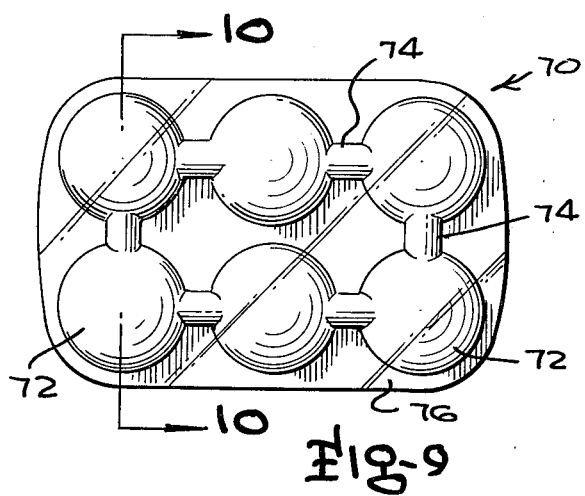
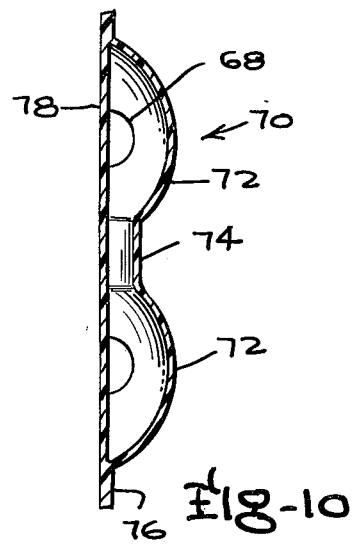
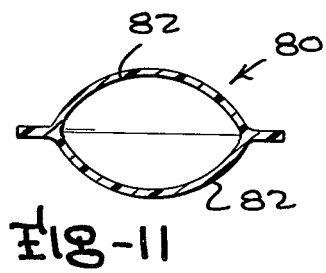
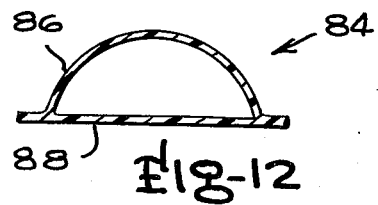
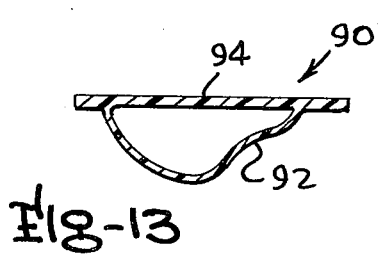
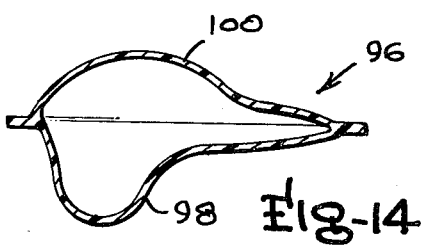

EYE BANDAGE

BACKGROUND OF THE INVENTION

This invention relates to bandages and more particularly relates to a pneumatic eye bandage which can be used to protect the eye of the user from external mechanical trauma and infection, prevent movement of the eyelid, collect discharges from the eye, or decrease the amount of light entering the eye.

Ophthalmic patches or eye bandages are commonly used to protect the eye of a patient from external infection, from external mechanical trauma, from bright light, from perceiving images which might induce unwanted eye movement, to collect discharge from the conjunctiva, and the like.

It is common practice in the medical profession to form eye bandages for most of such cases by applying an absorbent cotton or rayon pad with gauze surfaces over the eyelid of the patient with separate pieces of adhesive tape attached to the forehead and cheek. A perforated metal shield is often applied over the absorbent pad to exert desired pressure against the eye and the eyelid. These presently known bandages fail to conform well to the irregular shape and surface of the eyelid, orbital margin, and face and thus fail to provide adequate protection for these very sensitive areas. Since the absorbent pad does not adhere to the eyelids, these presently known bandages can result in scratching of the cornea. Furthermore, these bandages are usually constructed of heavy materials which result in discomfort to the user. The application of these bandages to the eye of the user is time consuming because of the multiplicity of parts and the difficulty inherent in achieving a uniform pressure on the eyelid and the eye of the user due to the irregular depth and face plane shape of the orbit of the user. Inadequate protection against external mechanical trauma and the frequent need to supplement the bandage with a metal shield which is neither inexpensive nor disposable are additional difficulties with the present known eye bandages. Additionally, these eye bandages are difficult even for trained persons to fashion into a semi-pressure patch. These semi-pressure patches as previously made often result in inadequate and nonuniform pressure which delays recovery of the patient and usually results in a waste of eye pads and tape in attempting to create a satisfactory eye bandage. Also, the formation and application of these previous semi-pressure patches has required the time of more highly trained and expensive personnel. The current eye bandages require the preparation and handling of from three to as many as ten individual pieces of absorbent pad and tape.

The present invention provides improved results over the presently known eye bandages through the provision of pneumatic cells of various configurations contained between an absorbent eye pad and a unitary, flexible outer cover panel having adhesive coated areas. Adhesive may be applied to the eye pad or pneumatic cells if it is desired to prevent movement of the eyelid relative to the bandage.

Therefore, it is the primary object of this invention to provide a new and improved eye bandage.

Another object of the present invention is the provision of an eye bandage having an eye pad which provides improved conformation to the eye of the user.

A further object of the present invention is the provision of a new and improved eye bandage for protecting the eye of the user from external mechanical trauma without requiring the incorporation of a metal shield.

An additional object of the present invention is to provide an eye bandage which applies uniform pressure on the upper eyelid of the user when a semi-pressure patch is desired.

A still further object of the present invention is to decrease the quantities of materials which are required in the construction of an eye bandage, which decreases the length of time required to correctly apply the eye bandage, and which decreases the level of training required to properly apply eye bandages.

The objects of this invention are achieved through the provision of an outer cover panel having an adhesive portion at each end and a centrally positioned pneumatic cushion which may optionally be provided with an attached absorbent eye pad, if desired, and which effectively covers the eyelid of the user. The pneumatic cushion may be composed of multiple cells or a single cell and may be of various conforming configurations and levels of rigidity to accomplish the various clinical uses to which the subject invention is applicable. For example, a preferred embodiment has an upper cell which is contoured to conform to the upper eyelid of the user and a lower cell contoured to conform to the lower eyelid. Other embodiments include multiple cells which are interconnected by air passageways and multiple cells which are independent. Additional embodiments include cells which are symmetrical in shape such as semi-spherical or cup shape and cells which are asymmetrical to achieve desired pressure distributions. Additionally, adhesive may be applied instead of an absorbent eye pad or in addition to a portion of the eye pad to control or prevent movement of the eyelids of the user.

A better understanding of the manner in which the preferred embodiments of the subject invention achieve the objects of the invention will be enabled when the following written description is read in conjunction with the appended drawings in which:

FIG. 1 is an elevation view of a preferred embodiment of the present invention showing the eye bandage applied to the eye of the user;

FIG. 2 is an enlarged vertical section view of the embodiment of the present invention shown in FIG. 1;

FIG. 3 is an expoloded perspective view of the embodiment of the present invention shown in FIG. 1;

FIG. 4 is a perspective view of the FIG. 3 embodiment shown in packaged form in a transparent shipping container and including protective strips for the adhesive areas;

FIG. 5 is a rear view of the eye bandage shown in FIG. 3;

FIG. 6 is an enlarged sectional view of the packaged eye bandage taken along line 6—6 of FIG. 4;

FIG. 7 is an exploded perspective view of a single cell pneumatic cushion and an absorbent pad to be attached thereto;

FIG. 8 is a perspective view of an alternate pneumatic cushion having multiple cells;

FIG. 9 is a front view of an alternate pneumatic cushion having multiple interconnected cells;

FIG. 10 is a vertical sectional view along line 10—10 of FIG. 9;

FIG. 11 is a sectional view of an alternate pneumatic cushion formed with two symmetrical convex sides;

FIG. 12 is a sectional view of an alternate pneumatic cushion formed with a symmetrical convex side and a flat side;

FIG. 13 is a sectional view of an alternate pneumatic cushion formed with an asymmetrical outwardly curving side and a flat side;

FIG. 14 is a sectional view of an alternate pneumatic cushion formed with two asymmetrical outwardly curving sides.

Referring to the drawings wherein like references characters designate corresponding parts throughout the several figures and particularly to FIGS. 1 and 2, the eye bandage is indicated generally by reference character 20 and includes an outer cover panel or carrier panel 22 having a pair of wings or extensions to be fastened to the facial surface of the patient, an inner pneumatic cushion formation 24 at the center portion of the panel 22, a pad 26 which may either be absorbent or adhesive, an adhesive pad 28, and protective strips 30.

To enable attachment of the eye bandage to the face of the user as shown in FIGS. 1 and 2, outer cover panel 22 has adhesive areas 32 and 34 adjacent the opposite ends of the panel 22 flanking the pneumatic cushion formation 24 to adhesively secure the bandage to the facial surface. The cover panel 22 may be formed of a fabric such as cotton or a plastic film which is preferably elastic and air permeable to provide good conformance to the contour of the face of the user and to permit air to circulate around the bandage.

The pneumatic cushion formation 24 in the preferred embodiment, as shown in FIGS. 1 through 6, has an upper eye lid air cell 36 and a lower eye lid air cell 38 which are formed by bonding a thin flexible flat backing sheet 40 to a front sheet 42 of similar material shaped as illustrated to provide the upper eye lid air cell 36 and the lower eye lid air cell 38. The pneumatic cushion formation is secured to the outer cover panel 22 by a bonding adhesive area 44 shown in FIG. 3.

The pneumatic cushion formation 24 may be formed of sheets of an air impervious thin plastic sheet material such as vinyl thermally shaped and bonded together to produce a pair of air cells 36, 38 of the configuration shown to bear against the upper and lower eye lids and tend to hold them closed. An absorbent pad 26 may be adhered or otherwise located on the rearwardly facing surface of air cell 38, and is formed of cotton gauze or any other absorbent material such as rayon. Alternatively, an adhesive area may be provided on this rear surface of the lower air cell 38 to adhere to the patient's lower eye lid and hold it against opening movement. The adhesive areas 32, 34, and 44 may be formed by coating panel 22 with any conventional adhesive material.

The removable protective strips 30 cover the adhesive areas 32 and 34, the pad 26 and adhesive pad 28 as shown in the FIGS. 3, 4 and 6 until the bandage is applied. The strips 30 may be formed of a thin, relatively stiff plastic material to make the strips 30 easily removable when desired.

The eye bandage is preferably packed in a transparent container 46 including a flat back panel 48 and a hollow front panel 50 which is bonded around its edges to the flat back panel to form an air tight sterile container for the eye bandage. The transparent container 46 is preferably formed of a semi-rigid plastic material for ease of handling.

Various alternate embodiments of the pneumatic cushion formation 24 which may be mounted on the outer cover panel 22 in place of the dual cell cushion formation of FIGS. 1 through 6 are shown in FIGS. 7 through 14. All of the pneumatic cushions are similarly formed of two sheets of a flexible plastic sheet material such as vinyl or the like with at least one of the sheets shaped to define preformed cells to provide the desired configuration. The air cells are formed by bonding, as by thermal welding, the two sheets together in the desired areas as shown in the various figures to provide closed air cells which remain inflated during the period of use of the bandage thereby providing the desired pneumatic cushion.

A single air cell cushion 52 is shown in FIG. 7 and is formed by bonding a circular backing sheet 54 to the marginal edges 56 of a shallow cup front sheet 58. In the illustrated embodiment, a single cell absorbent pad 60 formed of an absorbent gauze material or the like is supported against the single air cell cushion 52 to engage the patient's eye lids. The cell with pad is mounted on an outer cover panel similar to the panel 22 shown in FIG. 3. All of the remaining embodiments of the air cells shown in the remaining figures are mounted in similar fashion on the outer cover panel.

A multiple independent air cell cushion 62 is shown in FIG. 8, having plural air cells 64 which are not pneumatically interconnected. Each independent air cell 64 is substantially semispherical in shape and is preformed in an independent cell front sheet 66 which is bonded to a complimentary back sheet 68 adjacent the bases of the semi-spherical cells portions to form the independent air cells 64. This configuration enables the application of high pressure to the areas where the centers of the spherical surfaces of the cells 64 contact the surfaces adjacent the eye of the user.

FIGS. 9 and 10 show a multiple interconnected air cell cushion 70 in which the air cells 72 are interconnected by air passageways 74. This cushion 70 has six multiple interconnected cells 74 formed between a front sheet 76 and a backing sheet 78. The cells are preformed to a configuration such that each has a generally semi-spherical shape and communicates with the air passageways 72 formed simultaneously with the semispherical cells. This cushion prevents localized high pressure against portions of the eye lid or face of the patient because the pressure is distributed to all 6 cells.

A double convex symmetrical pneumatic cushion 80 is shown in FIG. 11, formed with two identical generally semi-spherical preform sheets 82 which are jointed by thermal bonding or the like around the base of the preform sheets. This cushion permits the applications of relatively high pressure to a desired area of the eye depending on where it is positioned.

A flat backed symmetrical pneumatic cushion 84 is shown in FIG. 12 which is similar to the single air cell cushion 52 shown in FIG. 7 except cushion 84 has a preformed semi-spherical convex flat or outer sheet 86 and a circular flat front sheet 88 which is similar to circular backing sheet 54 and is bonded around its periphery to the periphery of the semi-spherical sheet 86.

A flat backed asymmetrical air cell cushion 90 is shown in FIG. 13 which is similar to upper cell 36 shown in the embodiment of FIGS. 1 through 6 except it has an irregular asymmetrical convex contoured inner sheet 92 to achieve a desired pressure distribution bonded to an outer flat backing sheet 94 to form this cushion.

Another embodiment of the pneumatic cushions depicted in the figures is a double asymmetrical air cell cushion 96 shown in FIG. 14. This cell has two asymmetrically contoured convex sheets 98 and 100 which are bonded together around their edges to form the double asymmetrical air cell 96.

When needed, an eye bandage having aa pneumatic cushion of the desired configuration is removed from the outer package or container 46 and the protective strips 30 are pulled back away from the absorbent or adhesive pad 26, if present and from the adhesive pad 28. The eye bandage is then positioned over the eye of the patient as shown in FIGS. 1 and 2 to place the absorbent adhesive pad 26 and the adhesive pad 28 in a proper position contacting the eye lids of the patient. The protective strips 30 are pulled off the adhesive areas 32 and 34 and the adhesive areas are pressed against the skin of the patient as shown in FIG. 2 to firmly attach the eye bandage in the desired position.

Any of the pneumatic cushions shown in the various figures may be utilized with or without adhesive pads or absorbent pads depending on the desired application. If light must be excluded from the eye of the patient, an opaque material is preferably used for the outer cover panel 22 thereby preventing any light from entering the eye of the patient.

As can be seen, the present invention provides a convenient and easily applied eye bandage.

It is to be understood that numerous modifications of the disclosed embodiments of the subject invention will undoubtedly occur to those of skill in the art and the spirit and scope of the invention is to be limited solely in light of the appended claims. For example, backing sheet 40 may be eliminated by bonding front sheet 42 directly to the outer cover panel 22.

I claim:

1. An eye bandage for protecting the eye of a patient comprising a unitary, flexible outer cover panel and a pneumatic cushion centrally positioned on the outer cover panel and formed of a flexible thin impervious material for defining at least one air cell having a flexible wall positioned adjacent the eye of the patient, said cover panel having adhesive surface portions laterally adjacent the cushion for attachment to the facial surface surrounding the eye of the patient.

2. The eye bandage of claim 1 additionally including an absorbent pad intermediate the pneumatic cushion and the eye of the patient to collect any discharges from the eye of the patient.

3. The eye bandage of claim 1 wherein the pneumatic cushion is contoured to conform to the area adjacent the eye of the patient thereby achieving a desired pressure distribution when the bandage is applied to the eye of the patient.

4. The eye bandage of claim 1 wherein the pneumatic cushion comprises an upper pneumatic cell which is contoured to conform to a portion of the upper eyelid of the patient and a lower pneumatic cell contoured to conform to a portion of the lower eyelid of the patient.

5. The eye bandage of claim 4 wherein the transverse area of the upper pneumatic cell has an upwardly arching crescent shape whose lower edge is of larger radius than its upper edge and the transverse area of the lower cell has a generally elongated elliptical shape in partially nesting relation to the curve defined by said lower edge thereby providing an eye bandage with a pneumatic cushion which conforms to the upper and lower eyelid of the patient.

6. The eye bandage of claim 1 wherein the pneumatic cushion comprises a single closed air cell.

7. The eye bandage of claim 6 wherein the single closed air cell has a front and a back sheet member formed of thin flexible plastic material with said sheet members peripherally bonded to one another around their edges to form the closed cell and said outer panel cover has a central portion larger than the transverse area of the air cell and is secured to and outwardly overlying the air cell.

8. The eye bandage of claim 1 wherein the pneumatic cushion comprises a multiplicity of closed air cells.

9. The eye bandage of claim 8 wherein the air cells comprise a flat back sheet member formed of a thin flexible plastic material bonded to a preformed front sheet member having four semi-spherical pockets and said outer panel cover has a central portion larger than the transverse area of the air cells and is secured to and outwardly overlying the air cells.

10. The eye bandage of claim 1 wherein the pneumatic cushion comprises a multiplicity of pneumatically interconnected air cells.

11. The eye bandage of claim 10 wherein the interconnected air cells comprise a flat back sheet member formed of a thin flexible material bonded to a preformed front sheet member of a thin flexible material having six semi-spherical pockets pneumatically interconnected by air passageways and said outer panel cover has the air cells and is secured to and outwardly overlying the air cells.

12. An eye bandage for protecting the eye of the patient comprising a pneumatic cushion formed of a pair of flexible thin sheets of air impervious material joined together to define at least one air cell having flexible walls, an eyelid adhesive means on the pneumatic cushion for attaching the eyelid of the user to the pneumatic cushion, an absorbent pad intermediate the pneumatic cushion and the eye of the patient, and an overlying unitary, flexible outer cover panel having a central portion larger than the transverse area of the pneumatic cushion secured to and outwardly overlying the pneumatic cushion for retaining the pneumatic cushion in pressure contact with the eyelid of the user, said cover panel having adhesive surface portions laterally adjacent the cushion to enable attachment of the eye bandage to the facial surface surrounding the eyelid of the patient.

13. The eye bandage of claim 12 wherein the pneumatic cushion is contoured to conform to the area adjacent the eye of the patient thereby achieving a desired pressure distribution when the bandage is applied to the eye of the patient.

14. The eye bandage of claim 12 wherein the pneumatic cushion comprises an upper pneumatic cell which is contoured to conform to a portion of the upper eyelid of the patient and a lower pneumatic cell contoured to conform to a portion of the lower eyelid of the patient and wherein the absorbent pad is positioned on the lower cell and the eyelid adhesive means is positioned on the upper cell.

15. The eye bandage of claim 14 wherein the transverse area of the upper pneumatic cell has an upwardly arching crescent shape whose lower edge is of larger radius than its upper edge and the transverse area of the lower cell has a generally elongated elliptical shape in partially nesting relation to the curve defined by said lower edge thereby providing an eye bandage with a pneumatic cushion which conforms to the upper and lower eyelid of the patient.

16. The eye bandage of claim 12 additionally including a protective strip attached to and separable from the adhesive surface portions of the cover panel thereby preventing the bandage from adhering to any surface until the protective strip is removed.

17. The eye bandage of claim 12 wherein the pneumatic cushion comprises a multiplicity of pneumatically interconnected air cells having a flat back sheet member formed of a thin flexible plastic material bonded to a preformed front sheet member formed of a thin flexible plastic material and having a multiplicity of semi-spherical pockets interconnected by air passageways.

18. The eye bandage of claim 12 wherein the pneumatic cushion comprises a single closed air cell having a front and a back sheet member formed of a thin flexible plastic material with said members peripherally bonded to one another around their edges to form the closed cell.

19. The eye bandage of claim 1 wherein the outer cover panel is formed of an opaque material.

* * * * *